United States Patent [19]

Rogers et al.

[11] 4,013,038

[45] Mar. 22, 1977

[54] APPARATUS FOR CONTROLLING THE TEMPERATURE OF A LIQUID BODY

[75] Inventors: Charles H. Rogers; Kevin J. Sullivan; Miles E. Vance, all of Raleigh, N.C.

[73] Assignee: Corning Glass Works, Corning, N.Y.

[22] Filed: July 21, 1975

[21] Appl. No.: 597,323

[52] U.S. Cl. .................................. 118/5; 118/64; 118/314; 34/48; 73/336.5; 73/338
[51] Int. Cl.² .......................................... B05C 5/00
[58] Field of Search .............. 73/338, 336.5, 339 C, 73/77; 118/5, 314, 64, 58; 34/46, 48

[56] References Cited
UNITED STATES PATENTS

| | | | |
|---|---|---|---|
| 2,154,927 | 4/1939 | Yaglou | 73/339 C X |
| 3,070,459 | 12/1962 | Schaffer | 118/66 X |
| 3,391,670 | 7/1968 | Lester et al. | 118/58 X |
| 3,771,364 | 11/1973 | Worthington | 73/338 X |

Primary Examiner—John P. McIntosh
Attorney, Agent, or Firm—William J. Simmons, Jr.; Walter S. Zebrowski; Clarence R. Patty, Jr.

[57] ABSTRACT

Apparatus for controlling the temperature of an open liquid body when actual measurement of that temperature is not possible. A thermal analog of the liquid body, which is exposed to the same heating or cooling source as the liquid body, is incorporated into a sensor which provides controlling feedback to the heating or cooling source. The sensor, which is disposed in the atmosphere which surrounds or flows by the liquid body, includes a dry element and a wet wick, body of which are in thermal contact with a temperature sensing element. The dry element senses the temperature of the atmosphere and the wet wick has a cooling effect on the sensing element that is related to the rate of evaporation of liquid from the body. This sensor is advantageously employed in a system for regulating the temperature of a reagent film on a microscope slide.

16 Claims, 7 Drawing Figures

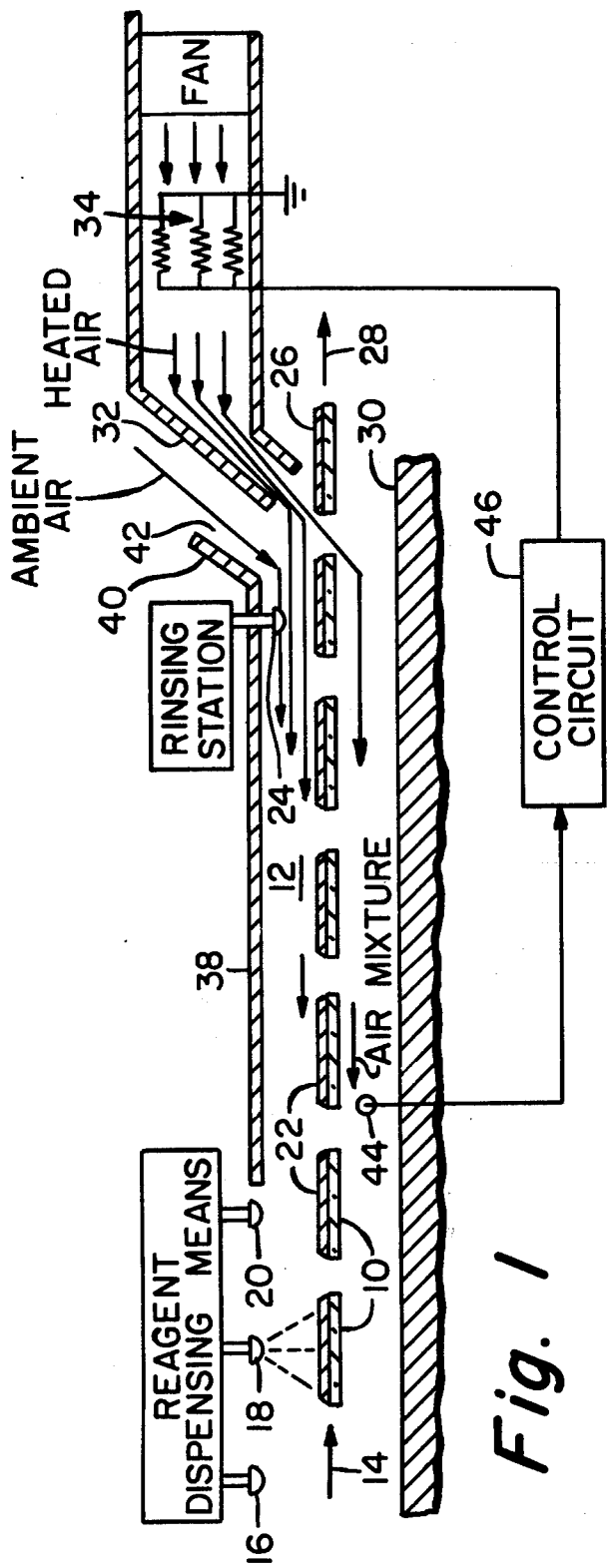
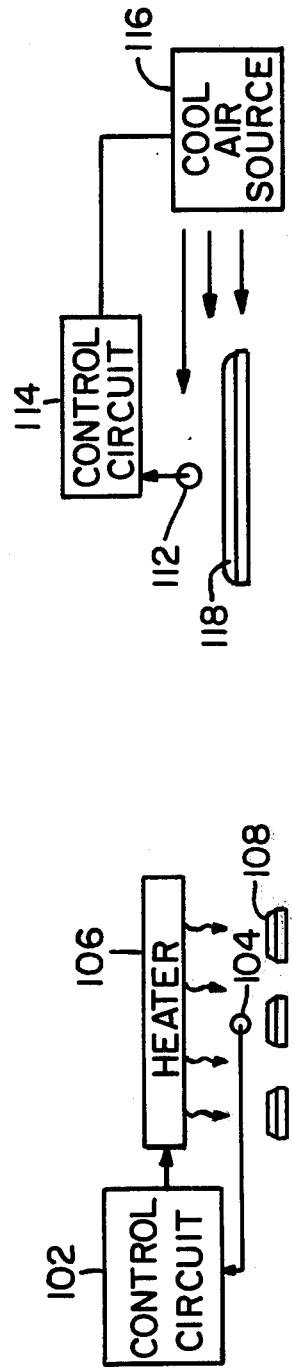

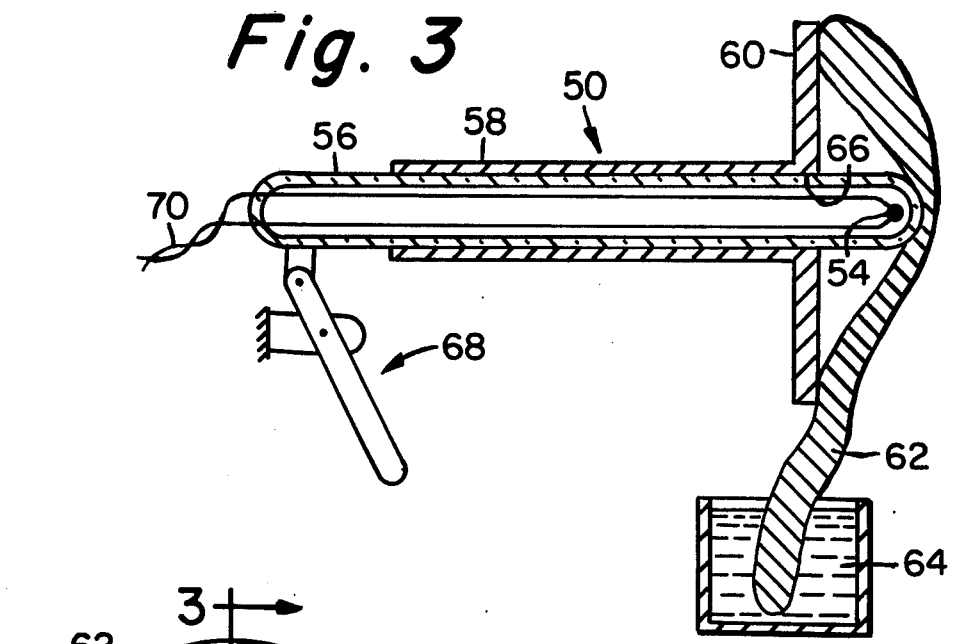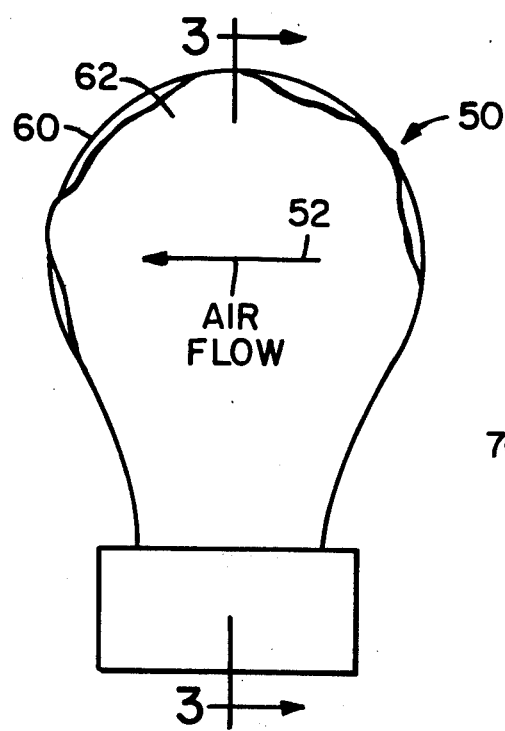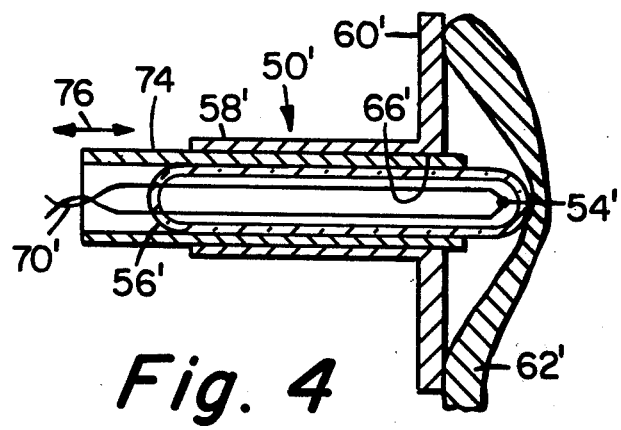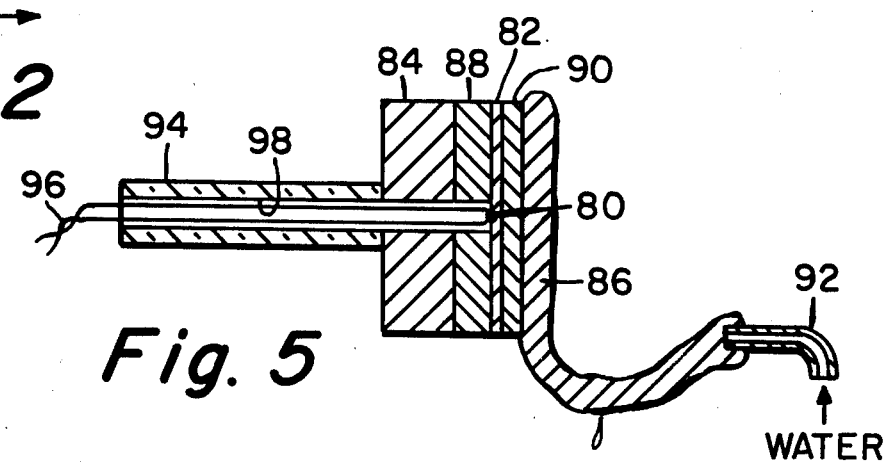

APPARATUS FOR CONTROLLING THE TEMPERATURE OF A LIQUID BODY

BACKGROUND OF THE INVENTION

This invention relates to temperature sensors and more particularly to sensors for determining the temperature of an open liquid body without making actual contact with that body. This invention is advantageously employed in conjunction with microscope slide staining apparatus of the type wherein a reagent film disposed on the surface of the slide must be maintained at a temperature within a predetermined range for a predetermined period of time to achieve optimal optical density and contrast.

In the microscopic examination of certain material, particularly cellular materials such as blood, tissue, or the like, a specimen of the material is placed on a transparent microscope slide. Thereafter, the material is stained by contacting it with solutions which stain or dye only certain constituents of the cell to provide a contrast which facilitates examination. Mechanized means are being increasingly employed for staining microscope slides. This type of apparatus conveys the slides through a plurality of stations where the staining reagents are automatically applied to the specimen. One such automatic staining apparatus is disclosed in U.S. Pat. No. 3,853,092 issued to L. G. Amos et al. This apparatus conveys the microscope slides in a circular path and automatically dispenses a metered amount of various reagents on the upper surface of the slides. The apparatus also imparts a nutating motion to the slide to effect uniform wetting of the top surface thereof by each reagent and by the rinse. The slides are thereafter moved to a near vertical position for draining and drying.

By controlling the time during which the specimen is subjected to each reagent and by carefully metering the amount of reagents applied, it is possible to obtain stained specimens exhibiting sufficient contrast for visual analysis. For example, laboratory technicians can perform what is referred to as a white blood cell differential by counting the leukocytes on a stained blood smear. Because of the amount of time required for a technician to analyze a biological specimen and due to the increasing number of analyses being performed, automation of tests such as the white blood cell differential is inevitable. A thesis by J. W. Bacus, "An Automated Classification of the Peripheral Leukocytes by Means of Digital Image Processing", University of Illinois, Chicago, 1971, describes one automated system. A system for automatically scanning and digitizing the count of leukocytes on a stained smear is disclosed in copending application Ser. No. 353,004 entitled "Image Scanning Converter for Automated Slide Analyzer" filed by D. A. Cotter on Apr. 20, 1973, now U.S. Pat. No. 3,883,852.

The accuracy with which automated slide analysis can be performed depends upon the reproducibility of the slide staining process. Each blood film, for example, should be stained so that the optical density of a given type of nucleus substantially achieves a specified value. Furthermore, the staining process should provide optimal contrast between the cell nucleus and cytoplasm. Apparatus capable of improving the reproducibility of the slide staining process is disclosed in U.S. Patent Application Ser No. 597,442 entitled "Microscope Slide Staining Apparatus Having Temperature Control" filed by C. H. Rogers et al. on even date herewith. The apparatus of that application comprises means for forming a film of staining reagents on the surface of a slide and heating means for flowing heated air over the surface of the reagent film. To maintain the film temperature within a predetermined range, a temperature sensor is employed to measure the temperature of the atmosphere surrounding the reagent film, and the sensor output controls the heating means. However, the film temperature is determined by a balance of the heating effect of the warm air and the cooling effect of evaporation from the film surface. The magnitude of this cooling effect is a strong function of ambient relative humidity; consequently, the film temperature cannot be regulated to the desired extent by simply holding the warm air temperature constant.

SUMMARY OF THE INVENTION

Briefly, the present invention specifically relates to a non-contacting temperature sensor for determining the temperature of a liquid body disposed in an atmosphere. The sensor comprises a temperature sensing element which provides an electrical signal related to the temperature thereof, a dry, thermal conductor in thermal contact with the sensing element and a wet wick in thermal contact with the sensing element.

This temperature sensor is advantageously employed in an apparatus for maintaining the temperature of an open liquid body within a predetermined range. The electrical signal provided by the sensor provides a controlling feedback to a heating or cooling source to which the liquid body and the sensor are exposed.

In a specific embodiment of the present invention the liquid body is a reagent film disposed on the upper surface of a microscope slide having a biological specimen thereon. Heating means are provided for increasing the temperature of the reagent film and the electrical signal from the sensor controls the heat energy output of the heating means.

BRIEF DESCRIPTION OF THE DRAWINGS

FIG. 1 is a schematic illustration in partial section, of a system embodying the sensor of the present invention.

FIG. 2 is a plan view of a sensor constructed in accordance with the present invention.

FIG. 3 is an elevation, partly in section, of the sensor of the present invention taken along lines 3—3 of FIG. 2.

FIGS. 4 and 5 are cross-sectional views of further embodiments of the sensor of the present invention.

FIGS. 6 and 7 are schematic illustrations in block diagram form of further systems embodying the sensor of the present invention.

DESCRIPTION OF THE PREFERRED EMBODIMENTS

FIG. 1 is a schematic illustration of a microscope slide staining apparatus. Microscope slides 10 are conveyed through a chamber 12 by any suitable means (not shown) such as a conveyor belt or individual rotating supports of the type disclosed in the aforementioned Amos et al. patent. As slides 10 move in the direction of arrow 14, they pass under nozzles 16, 18 and 20 which dispense staining reagents that form a film 22 on the slide surface. For the treatment of a microscope blood slide, such reactants may be a fixative, dye and buffer. After all of the desired reactants are dispensed upon the top surface of a slide, they are permitted to act upon the specimen for a predetermined period of time until the slide is rinsed by a solution such as water that is dispensed from nozzle 24. The slides having a water film 26 on the surface thereof then continue to be conveyed in the direction of arrow 28. Any excess water or reagents liquid is collected in drain bowl 30. The rinsed slides may be manually removed from the conveying means, or they may be dried and automatically removed by means such as that disclosed in said Amos et al. patent.

As discussed in said copending Rogers et al. patent application, reagent film temperature is one of the parameters that must be controlled to obtain reproducible stain uptake, that temperature preferably being maintained between 24° and 37° C to enhance the contrast between the cell nucleus and cytoplasm. The reagent films disposed upon the upper surfaces of the slides being conveyed between the last reagent dispensing nozzle 20 and rinse nozzle 24 are heated by warm air flowing from duct 32. The heated air is generated by blowing ambient air over resistance heater coils 34.

Since duct 32 is disposed along chamber 12 after the rinsing station, air flowing therefrom initiates the process of drying the slide surfaces. To more efficiently start the drying process, the temperature of the air from duct 32 is higher than the optimal temperature range for the reagent film on those slides prior to the rinsing station. Warm air duct 32 is therefore so disposed that ambient air is entrained with the warm air flowing therefrom, and it is this mixture of warm and ambient air which heats the reagent films to the desired temperature. Cover 38 may be provided with an air scoop 40 adjacent to duct 32 to provide a channel 42 through which entrained ambient air flows.

To control the temperature of the reagent films, the apparatus disclosed in the aforementioned Rogers et al. patent application employs a temperature sensor 44, which is disposed in chamber 12 as close to reagent films 22 as is practicable. As the air mixture formed by the heated air and the ambient air entrained therewith flows over and heats reagent films 22, the temperature of the air mixture is sensed by sensor 44. A control signal is supplied by sensor 44 to control circuit 46 which regulates the power supplied to heating coils 34, thereby maintaining the temperature of the warm air mixture in chamber 12 within a predetermined range of temperatures.

However, the temperature of reagent films 22 is determined by the balance of the heating effect of the heated air and the cooling effect of evaporation from the film surface. The magnitude of this cooling effect is a strong function of ambient relative humidity; consequently, the film temperature cannot be regulated by simply holding the warm air temperature constant. A sensor for providing an indication of the temperature of the reagent films without actually contacting those films is illustrated in FIGS. 2 and 3. Sensor 50 is adapted to be positioned in the vicinity of the slides being stained, the same air mixture that is heating the reagent films flowing in the direction indicated by arrow 52. A sensing element 54, which may be a thermocouple, heat-sensing resistor or the like, is disposed in a tubular envelope 56 which is made of glass, plastic, metal or the like. Envelope 56 extends through a sleeve 58 which is in thermal contact with a dry disc 60. Sleeve 58 and disc 60 may consist of any heat conductive material such as copper, aluminum, or a high thermal conductivity glass or plastic or the like. A portion of a wick 62 is disposed adjacent to one face of disc 60 and is attached to that face at the circumference of the disc by any suitable means such as bonding material or a clip (not shown). An end of wick 62 is submersed in a suitable liquid 64. The sensor functioned satisfactorily when water was used as the liquid employed to wet wick 62. The end of tube 56 containing element 54 protrudes from a hole 66 in disc 60 and contacts wick 62.

Since the same air flow which heats the reactant films passes parallel to the disc surface, disc 60 and sleeve 58 are heated by the warm air mixture and the wick is cooled by evaporation. The relative proportion of each of these two effects can be adjusted by varying the thermal conductivities between the sensing element and the wet and dry parts of the sensor. In FIG. 3, this adjustment is performed by actuating a lever system 68 which causes tube 56 to slide within sleeve 58. By properly positioning element 54 with respect to disc 60, the sensor can be made to respond to changes in air temperature and relative humidity in the same manner as the reactant film responds to these ambient conditions. The sensor can thus be made to act as a thermal analog of the reagent film on the microscope slides, and the electrical signal appearing on leads 70 provides an accurate indication of film temperature.

Another embodiment of the present invention is illustrated in FIG. 4 wherein elements similar to those of FIGS. 2 and 3 are represented by primed reference numerals. In this embodiment a heat conductive tube 74 is slidably mounted between envelope 56' and sleeve 58' so that it is free to move in the direction of arrow 76. When tube 74 is moved closer to sensing element 54' it conducts more heat from disc 60' to that element. Proper adjustment of tube 74 causes sensor 50' to provide an output signal on leads 70' which is indicative of the temperature of the reagent films.

In the embodiment illustrated in FIG. 5 temperature sensing element 80 is affixed to a disc or sheet 82 of high thermal conductivity material. Element 80 may, for example, be embedded in disc 82, or it may be bonded thereto by thermally conductive bonding material. If element 80 is disposed within a tubular envelope as described in conjunction with the embodiments of FIGS. 3 and 4, an end of that envelope may be affixed to disc 82. Dry disc 84 of high thermal conductivity material, such as metal, plastic, glass or the like, and wet wick 86 are separated from disc 82 by discs 88 and 90, respectively, of intermediate thermal conductivity material such as plastic, glass or the like. It is known that some glasses and plastics have relatively low thermal conductivities while other glasses and plastics have relatively high thermal conductivities. Moreover, the conductivity of a given plastic material may be increased by loading it with a conductive substance such as metallic powder. Thus, elements 82, 84, 88 and 90 could all consist of plastic, for example, provided that the thermal conductivity of the material from which elements 82 and 84 are formed is greater than that of the material from which elements 88 and 90 are formed. Either of the discs 88 or 90 could be omitted to provide increased thermal conductance between element 80 and disc 84 or wick 86, respectively. For example, increased conductance between wick 86 and element 80 could be obtained by omitting disc 90 and affixing wick 86 directly to disc 82.

The sensor is supported by a thermally insulating support member 94. Electrical leads 96 from the sensing element extend through holes in discs 84 and 88 and through feed through hole 98 in member 94.

FIG. 5 also illustrates an alternate method of wetting the wick. In accordance with this method a portion of wick 86 hangs between the sensor and a fitting 92 which periodically feeds water to the wick. The excess water drips from the lowest point on the wick, thereby maintaining a constant wetness at the sensor.

The sensor of FIG. 5 is positioned near the slides being stained, the same air or gas mixture employed to heat the reagent films flowing past the sensor. The temperature of element 80 is determined by the temperatures of wick 86 and disc 84 and the relative thermal conductances of discs 88 and 90 which are determined by disc thicknesses and the thermal conductivity of the disc material. Under convective heating or cooling, disc 84 assumes essentially the dry bulb temperature of the flowing gases while the wet wick assumes a wet bulb temperature appropriate to the vapor content, temperature and velocity of the flowing gases, the wick temperature also being related to the liquids with which it is wet. The conductances of discs 88 and 90 are selected to yield a sensing element temperature between the wet bulb and dry bulb temperatures. In particular, the conductances of discs 88 and 90 may be chosen so that the sensing element indicates the same temperature as that of a reagent covered slide exposed to the same flow of gases. In addition, these relative conductances can be chosen so that the sensing element temperature differs from the reagent temperature by a constant amount that is independent of the vapor content of the flowing gases. Typically, the flowing gases are atmospheric air, the vapor content of interest is water vapor content, and the wick is wet by water.

FIG. 6 illustrates a system wherein control circuit 102 is responsive to the output from sensor 104 to control the amount of heat energy radiated from radiant heater 106. Sensor 104 being of the type illustrated in FIGS. 2 through 5, the temperature of liquid films 108 can be accurately maintained regardless of the temperature and relative humidity of the surrounding atmosphere. In addition to the features discussed in conjunction with FIGS. 2 through 5, sensor 104 should have radiative properties matching those of the liquid film and its substrate. For example, if a stained biological specimen is disposed on the substrate, the sensor wick should be dyed a color to match that of the stained specimen.

In the embodiment illustrated in FIG. 7, a wet-dry temperature sensor 112 of the type illustrated in FIGS. 2 through 5 provides a signal to control circuit 114 which determines the temperature of the cool air which source 116 blows over sensor 112 and liquid film 118, thus controlling the liquid film temperature within a predetermined range.

Although the present invention has been described with respect to specific details of certain embodiments thereof, it is not intended that such details be limitations upon the scope of the invention except insofar as set forth in the following claims.

We claim:

1. An apparatus for staining a biological specimen disposed on the surface of a microscope slide comprising
   means for supporting said slide so that said biological specimen is disposed upon the upper surface thereof,
   means for dispensing a plurality of staining reagents on said upper surface of said slide to form a film of said reagents on said specimen, the surface of said film being exposed to a given atmosphere,
   a dry thermal conductor exposed to said given atmosphere,
   a wick exposed to said given atmosphere,
   means for applying to said wick a liquid having evaporative properties similar to those of said reagent film,
   a temperature sensing element in thermal contact with said dry thermal conductor and said wet wick for providing an electrical output determined by the temperature of said element,
   heating means for increasing the temperature of said reagent film, and
   control means responsive to the electrical output from said temperature sensing element for controlling the heat energy output of said heating means.

2. Apparatus in accordance with claim 1 further comprising means for varying the thermal conductances between said sensing element and said dry thermal conductor and between said sensing element and said wick.

3. An apparatus for staining a biological specimen disposed on the surface of a microscope slide comprising
   means for supporting said slide so that said biological specimen is disposed upon the upper surface thereof,
   means for dispensing a plurality of staining reagents on said upper surface of said slide to form a film of said reagents on said specimen, the surface of said film being exposed to a given atmosphere,
   a metallic disk having a hole therethrough, said disk being exposed to said given atmosphere,
   a wet wick exposed to said given atmosphere,
   a glass tube having first and second ends, said tube extending through the hole in said disk, the first end of said tube contacting said wet wick,
   a temperature sensing element being disposed in said first end of said tube and being in thermal contact with said metallic disk and said wet wick for providing an electrical output determined by the temperature of said element,
   a metallic sleeve in contact with said disk and surrounding at least a portion of the second end of said tube, said tube being slidably mounted within said sleeve,
   means for varying the thermal conductances between said sensing element and said disk and between said sensing element and said wet wick,
   heating means for increasing the temperature of said reagent film, and
   control means responsive to the electrical output from said temperature sensing element for controlling the heat energy output of said heating means.

4. An apparatus in accordance with claim 3 further comprising means for applying to said wick a liquid having evaporative properties similar to those of said reagent film.

5. An apparatus in accordance with claim 3 wherein a portion of said wick completely surrounds said first end of said glass tube and is affixed to said metallic disk around the entire circumference thereof.

6. An apparatus for staining a biological specimen disposed on the surface of a microscope slide comprising
 means for supporting said slide so that said biological specimen is disposed upon the upper surface thereof,
 means for dispensing a plurality of staining reagents on said upper surface of said slide to form a film of said reagents on said specimen, the surface of said film being exposed to a given atmosphere,
 a dry thermal conductor exposed to said given atmosphere,
 a wet wick exposed to said given atmosphere,
 a sheet of high thermal conductance material,
 a temperature sensing element in thermal contact with said dry thermal conductor and said wet wick for providing an electrical output determined by the temperature of said element, said temperature sensing element being affixed to said sheet,
 a mass of thermally conductive material having a thermal conductivity lower than the thermal conductivities of said sheet and said dry thermal conductor, said mass of thermally conductive material being disposed between said dry thermal conductor and said sheet,
 heating means for increasing the temperature of said reagent film, and
 control means responsive to the electrical output from said temperature sensing element for controlling the heat energy output of said heating means.

7. Apparatus in accordance with claim 6 wherein said wick and said sheet are separated by thermally conductive material having a thermal conductivity lower than the thermal conductivities of said sheet and said dry thermal conductor.

8. A temperature sensor for determining the temperature of a liquid body, the surface of which is exposed to a given atmosphere, said sensor comprising
 a temperature sensing element for providing an electrical signal representing the temperature of said element,
 a dry, thermal conductor in thermal contact with said element,
 a wick in thermal contact with said element, said dry thermal conductor and said wet wick being adapted to be exposed to said given atmosphere, and
 means for applying to said wick a liquid having evaporative properties similar to those of said liquid body.

9. A temperature sensor in accordance with claim 8 further comprising means for varying the thermal resistances between said sensing element and said dry thermal conductor and between said sensing element and said wick.

10. A temperature sensor for determining the temperature of a liquid body, the surface of which is exposed to a given atmosphere, said sensor comprising
 a temperature sensing element for providing an electrical signal representing the temperature of said element,
 a metallic disk having a hole therethrough, said disk being in thermal contact with said element,
 a wet wick in thermal contact with said element, said metallic disk and said wet wick being adapted to be exposed to said given atmosphere, and
 means for varying the thermal resistances between said sensing element and said metallic disk and between said sensing element and said wet wick, including
 a glass tube having first and second ends, said tube extending through the hole in said disk, the first end thereof contacting said wet wick, said sensing element being disposed in said first end of said tube, and a metallic sleeve in contact with said disk and surrounding at least a portion of the second end of said tube, said tube being slidably mounted within said sleeve.

11. A temperature sensor in accordance with claim 10 wherein a portion of said wick completely surrounds said first end of said glass tube and is affixed to said metallic disk around the entire circumference thereof.

12. A temperature sensor for determining the temperature of a liquid body, the surface of which is exposed to a given atmosphere, said sensor comprising
 a sheet of high thermal conductance material,
 a temperature sensing element affixed to said sheet for providing an electrical signal representing the temperature of said element,
 a dry, thermal conductor in thermal contact with said element,
 a mass of thermally conductive material having a thermal conductivity lower than the thermal conductivities of said sheet and said dry thermal conductor, said dry thermal conductor and said sheet being separated by said mass of thermally conductive material, and
 a wet wick in thermal contact with said element, said dry thermal conductor and said wet wick being adapted to be exposed to said given atmosphere.

13. A temperature sensor in accordance with claim 12 wherein said wick and said sheet are separated by thermally conductive material having a thermal conductivity lower than the thermal conductivities of said sheet and said dry thermal conductor.

14. A temperature sensor for determining the temperature of a liquid body, the surface of which is exposed to a given atmosphere, said sensor comprising
 a first disk of high thermal conductivity material,
 a temperature sensing element attached to said disk in a central portion thereof,
 a second disk of high thermal conductivity material, a portion of said second disk being adapted to be exposed to said given atmosphere, the thickness of said second disk being greater than that of said first disk,
 a third disk of thermally conductive material disposed between said first and second disks, the thermal conductivity of said third disk being lower than the thermal conductivities of said first and second disks, and
 a wet wick in thermal contact with said first disk, said wick being adapted to be exposed to said given atmosphere.

15. A temperature sensor in accordance with claim 14 further comprising a fourth disk of thermally conductive material disposed between said wick and said first disk, the thermal conductivity of said fourth disk being lower than the thermal conductivities of said first and second disks.

16. A temperature sensor in accordance with claim 15 wherein said second and third disks have holes through the central portion thereof, said temperature sensor further comprising a pair of lead wires extending from said temperature sensing element through said holes.

* * * * *